United States Patent
Turovskiy et al.

(10) Patent No.: US 8,663,213 B2
(45) Date of Patent: *Mar. 4, 2014

(54) REINFORCED HIGH STRENGTH MICROWAVE ANTENNA

(75) Inventors: Roman Turovskiy, San Francisco, CA (US); Ted Su, Sunnyvale, CA (US); Mani Prakash, Boulder, CO (US); Steven Kim, Los Altos, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/479,588

(22) Filed: May 24, 2012

(65) Prior Publication Data

US 2012/0232619 A1    Sep. 13, 2012

Related U.S. Application Data

(63) Continuation of application No. 13/214,503, filed on Aug. 22, 2011, now Pat. No. 8,192,423, which is a continuation of application No. 12/859,841, filed on Aug. 20, 2010, now Pat. No. 8,012,148, and a continuation of application No. 11/126,531, filed on May 10, 2005, now Pat. No. 7,799,019.

(51) Int. Cl.
    *A61B 18/18*    (2006.01)
(52) U.S. Cl.
    USPC ............................. 606/33; 606/41; 607/101
(58) Field of Classification Search
    USPC ............................. 606/33; 607/101, 102, 156
    See application file for complete search history.

(56) References Cited

U.S. PATENT DOCUMENTS

| 4,140,130 | A | 2/1979 | Storm, III |
| 4,204,549 | A | 5/1980 | Paglione |
| 4,292,960 | A | 10/1981 | Paglione |
| 4,311,154 | A | 1/1982 | Sterer et al. |
| 4,375,220 | A | 3/1983 | Matvias |
| 4,409,993 | A | 10/1983 | Furihata |
| 4,534,347 | A | 8/1985 | Taylor |
| 4,557,272 | A | 12/1985 | Carr |
| 4,583,869 | A | 4/1986 | Chive et al. |
| 4,612,940 | A | 9/1986 | Kasevich et al. |
| 4,621,642 | A | 11/1986 | Chen |
| 4,658,836 | A | 4/1987 | Turner |
| 4,700,716 | A | 10/1987 | Kasevich et al. |
| 4,776,086 | A | 10/1988 | Kasevich et al. |

(Continued)

FOREIGN PATENT DOCUMENTS

| EP | 0 521 264 | 5/1992 |
| EP | 0 667 126 | 8/1995 |

(Continued)

OTHER PUBLICATIONS

I Chou, C.K. (1995). "Radiofrequency Hyperthermia in Cancer Therapy," Biologic Effects of Nonionizing Electromagnetic Fields. Chapter 94, CRC Press, Inc. pp. 1424-1428.

(Continued)

*Primary Examiner* — Linda Dvorak
*Assistant Examiner* — Amanda Scott

(57) ABSTRACT

High-strength microwave antenna assemblies and methods of use are described herein. The microwave antenna has a radiating portion connected by a feedline to a power generating source, e.g., a generator. Proximal and distal radiating portions of the antenna assembly are separated by a junction member. A reinforcing member is disposed within the junction member to increase structural rigidity.

13 Claims, 8 Drawing Sheets

(56) References Cited

U.S. PATENT DOCUMENTS

| | | |
|---|---|---|
| 4,800,899 A | 1/1989 | Elliott |
| 4,823,812 A | 4/1989 | Eshel et al. |
| 4,841,988 A | 6/1989 | Fetter et al. |
| 4,945,912 A | 8/1990 | Langberg |
| 5,097,845 A | 3/1992 | Fetter et al. |
| 5,122,137 A | 6/1992 | Lennox |
| 5,190,054 A | 3/1993 | Fetter et al. |
| 5,221,269 A | 6/1993 | Miller et al. |
| 5,234,004 A | 8/1993 | Hascoet et al. |
| 5,246,438 A | 9/1993 | Langberg |
| 5,249,585 A | 10/1993 | Turner et al. |
| 5,275,597 A | 1/1994 | Higgins et al. |
| 5,281,217 A | 1/1994 | Edwards et al. |
| 5,301,687 A | 4/1994 | Wong et al. |
| 5,314,466 A | 5/1994 | Stern et al. |
| 5,342,355 A | 8/1994 | Long |
| 5,344,441 A | 9/1994 | Gronauer |
| 5,366,490 A | 11/1994 | Edwards et al. |
| 5,370,644 A | 12/1994 | Langberg |
| 5,370,676 A | 12/1994 | Sozanski et al. |
| 5,383,922 A | 1/1995 | Zipes et al. |
| 5,405,346 A | 4/1995 | Grundy et al. |
| 5,413,588 A | 5/1995 | Rudie et al. |
| 5,433,740 A | 7/1995 | Yamaguchi |
| 5,458,597 A | 10/1995 | Edwards et al. |
| 5,464,445 A | 11/1995 | Rudie et al. |
| 5,480,417 A | 1/1996 | Hascoet et al. |
| 5,500,012 A | 3/1996 | Brucker et al. |
| 5,507,743 A | 4/1996 | Edwards et al. |
| 5,509,929 A | 4/1996 | Hascoet et al. |
| 5,520,684 A | 5/1996 | Imran |
| 5,536,267 A | 7/1996 | Edwards et al. |
| 5,545,137 A | 8/1996 | Rudie et al. |
| 5,556,377 A | 9/1996 | Rosen et al. |
| 5,599,294 A | 2/1997 | Edwards et al. |
| 5,599,295 A | 2/1997 | Rosen et al. |
| 5,628,770 A | 5/1997 | Thome et al. |
| 5,683,382 A | 11/1997 | Lenihan et al. |
| 5,720,718 A | 2/1998 | Rosen et al. |
| 5,741,249 A | 4/1998 | Moss et al. |
| 5,755,754 A | 5/1998 | Rudie et al. |
| 5,776,176 A | 7/1998 | Rudie |
| 5,800,486 A | 9/1998 | Thome et al. |
| 5,810,803 A | 9/1998 | Moss et al. |
| 5,810,804 A | 9/1998 | Gough et al. |
| 5,829,519 A | 11/1998 | Uthe |
| 5,843,144 A | 12/1998 | Rudie et al. |
| 5,871,523 A | 2/1999 | Fleischman et al. |
| 5,897,554 A | 4/1999 | Chia et al. |
| 5,902,251 A | 5/1999 | vanHooydonk |
| 5,904,691 A | 5/1999 | Barnett et al. |
| 5,904,709 A | 5/1999 | Arndt et al. |
| 5,916,240 A | 6/1999 | Rudie et al. |
| 5,931,807 A | 8/1999 | McClure et al. |
| 5,931,860 A | 8/1999 | Reid et al. |
| 5,938,692 A | 8/1999 | Rudie |
| 5,951,547 A | 9/1999 | Gough et al. |
| 5,957,969 A | 9/1999 | Warner et al. |
| 5,964,755 A | 10/1999 | Edwards |
| 5,974,343 A | 10/1999 | Brevard et al. |
| 5,980,563 A | 11/1999 | Tu et al. |
| 5,997,532 A | 12/1999 | McLaughlin et al. |
| 6,016,452 A | 1/2000 | Kasevich |
| 6,016,811 A | 1/2000 | Knopp et al. |
| 6,026,331 A | 2/2000 | Feldberg et al. |
| 6,032,078 A | 2/2000 | Rudie |
| 6,047,216 A | 4/2000 | Carl et al. |
| 6,056,744 A | 5/2000 | Edwards |
| 6,059,780 A | 5/2000 | Gough et al. |
| 6,063,078 A | 5/2000 | Wittkampf |
| 6,073,051 A | 6/2000 | Sharkey et al. |
| 6,080,150 A | 6/2000 | Gough |
| 6,097,985 A | 8/2000 | Kasevich et al. |
| 6,106,518 A | 8/2000 | Wittenberger et al. |
| 6,122,551 A | 9/2000 | Rudie et al. |
| 6,134,476 A | 10/2000 | Arndt et al. |
| 6,146,379 A | 11/2000 | Fleischman et al. |
| 6,176,856 B1 | 1/2001 | Jandak et al. |
| 6,181,970 B1 | 1/2001 | Kasevich |
| 6,217,528 B1 | 4/2001 | Koblish et al. |
| 6,223,086 B1 | 4/2001 | Carl et al. |
| 6,226,553 B1 | 5/2001 | Carl et al. |
| 6,233,490 B1 | 5/2001 | Kasevich |
| 6,235,048 B1 | 5/2001 | Dobak, III |
| 6,245,064 B1 | 6/2001 | Lesh et al. |
| 6,251,128 B1 | 6/2001 | Knopp et al. |
| 6,275,738 B1 | 8/2001 | Kasevich et al. |
| 6,277,113 B1 | 8/2001 | Berube |
| 6,289,249 B1 | 9/2001 | Arndt et al. |
| 6,290,715 B1 | 9/2001 | Sharkey et al. |
| 6,306,132 B1 | 10/2001 | Moorman et al. |
| 6,325,796 B1 | 12/2001 | Berube et al. |
| 6,330,479 B1 | 12/2001 | Stauffer |
| 6,346,104 B2 | 2/2002 | Daly et al. |
| 6,347,251 B1 | 2/2002 | Deng |
| 6,350,262 B1 | 2/2002 | Ashley |
| 6,355,033 B1 | 3/2002 | Moorman et al. |
| 6,383,182 B1 | 5/2002 | Berube et al. |
| 6,405,733 B1 | 6/2002 | Fogarty et al. |
| 6,471,696 B1 | 10/2002 | Berube et al. |
| 6,496,736 B1 | 12/2002 | Carl et al. |
| 6,496,737 B2 | 12/2002 | Rudie et al. |
| 6,506,189 B1 | 1/2003 | Rittman, III et al. |
| 6,512,956 B2 | 1/2003 | Arndt et al. |
| 6,514,251 B1 | 2/2003 | Ni et al. |
| 6,530,922 B2 | 3/2003 | Cosman et al. |
| 6,564,806 B1 | 5/2003 | Fogarty et al. |
| 6,569,159 B1 | 5/2003 | Edwards et al. |
| 6,577,903 B1 | 6/2003 | Cronin et al. |
| 6,589,234 B2 | 7/2003 | Lalonde et al. |
| 6,592,579 B2 | 7/2003 | Arndt et al. |
| 6,640,139 B1 | 10/2003 | Ueberle |
| 6,663,624 B2 | 12/2003 | Edwards et al. |
| 6,675,050 B2 | 1/2004 | Arndt et al. |
| 6,685,700 B2 | 2/2004 | Behl et al. |
| 6,699,241 B2 | 3/2004 | Rappaport et al. |
| 6,706,040 B2 | 3/2004 | Mahon et al. |
| 6,722,371 B1 | 4/2004 | Fogarty et al. |
| 6,752,154 B2 | 6/2004 | Fogarty et al. |
| 6,752,767 B2 | 6/2004 | Turovskiy et al. |
| 6,823,218 B2 | 11/2004 | Berube |
| 6,852,091 B2 | 2/2005 | Edwards et al. |
| 6,878,147 B2 | 4/2005 | Prakash et al. |
| 7,128,739 B2 | 10/2006 | Prakash et al. |
| 7,147,632 B2 | 12/2006 | Prakash et al. |
| 7,174,217 B2 | 2/2007 | Rioux et al. |
| 7,190,989 B1 | 3/2007 | Swanson et al. |
| 7,207,985 B2 | 4/2007 | Duong et al. |
| 7,217,282 B2 | 5/2007 | Ginsburg et al. |
| 7,229,437 B2 | 6/2007 | Johnson et al. |
| 7,231,259 B2 | 6/2007 | Jenney et al. |
| 7,234,225 B2 | 6/2007 | Johnson et al. |
| 7,234,977 B2 | 6/2007 | Westlund et al. |
| 7,235,070 B2 | 6/2007 | Vanney |
| 7,238,166 B2 | 7/2007 | Callister |
| 7,238,184 B2 | 7/2007 | Megerman et al. |
| 7,238,194 B2 | 7/2007 | Monstadt et al. |
| 7,241,293 B2 | 7/2007 | Davison |
| 7,244,254 B2 | 7/2007 | Brace et al. |
| 7,245,955 B2 | 7/2007 | Rashidi |
| 7,264,619 B2 | 9/2007 | Venturelli |
| 7,270,656 B2 | 9/2007 | Gowda et al. |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,270,662 B2 | 9/2007 | Visram et al. |
| 7,271,363 B2 | 9/2007 | Lee et al. |
| 7,273,480 B2 | 9/2007 | Young et al. |
| 7,276,061 B2 | 10/2007 | Schaer et al. |
| 7,282,049 B2 | 10/2007 | Orszulak et al. |
| 7,285,116 B2 | 10/2007 | de la Rama |
| 7,293,562 B2 | 11/2007 | Malecki et al. |
| 7,300,438 B2 | 11/2007 | Falwell et al. |
| 7,301,131 B2 | 11/2007 | Gauthier et al. |

(56) References Cited

U.S. PATENT DOCUMENTS

| | | | |
|---|---|---|---|
| 7,306,592 B2 | 12/2007 | Morgan et al. |
| 7,309,325 B2 | 12/2007 | Mulier et al. |
| 7,309,336 B2 | 12/2007 | Ashley et al. |
| 7,311,702 B2 | 12/2007 | Tallarida et al. |
| 7,311,703 B2 | 12/2007 | Turovskiy et al. |
| 7,311,705 B2 | 12/2007 | Sra |
| 7,317,949 B2 | 1/2008 | Morrison et al. |
| 7,318,822 B2 | 1/2008 | Darmos et al. |
| 7,318,823 B2 | 1/2008 | Sharps et al. |
| 7,318,824 B2 | 1/2008 | Prakash et al. |
| 7,319,904 B2 | 1/2008 | Cross, Jr. et al. |
| 7,326,204 B2 | 2/2008 | Paul et al. |
| 7,326,205 B2 | 2/2008 | Paul et al. |
| 7,326,206 B2 | 2/2008 | Paul et al. |
| 7,331,957 B2 | 2/2008 | Woloszko et al. |
| 7,337,009 B2 | 2/2008 | Schell |
| 2001/0001819 A1 | 5/2001 | Lee et al. |
| 2001/0008966 A1 | 7/2001 | Arndt et al. |
| 2001/0020178 A1 | 9/2001 | Arndt et al. |
| 2001/0020180 A1 | 9/2001 | Arndt et al. |
| 2001/0037812 A1 | 11/2001 | Dobak, III et al. |
| 2002/0022832 A1 | 2/2002 | Mikus et al. |
| 2002/0087151 A1 | 7/2002 | Mody et al. |
| 2002/0133148 A1 | 9/2002 | Daniel et al. |
| 2002/0147444 A1 | 10/2002 | Shah et al. |
| 2002/0198520 A1 | 12/2002 | Coen et al. |
| 2003/0004506 A1 | 1/2003 | Messing |
| 2003/0065317 A1 | 4/2003 | Rudie et al. |
| 2003/0069578 A1 | 4/2003 | Hall et al. |
| 2003/0078573 A1 | 4/2003 | Truckai et al. |
| 2003/0088242 A1 | 5/2003 | Prakash et al. |
| 2003/0109862 A1 | 6/2003 | Prakash et al. |
| 2003/0195499 A1 | 10/2003 | Prakash et al. |
| 2004/0078038 A1 | 4/2004 | Desinger et al. |
| 2004/0167517 A1 | 8/2004 | Desinger et al. |
| 2004/0168692 A1 | 9/2004 | Fogarty et al. |
| 2004/0243200 A1 | 12/2004 | Turner et al. |
| 2004/0267156 A1 | 12/2004 | Turovskiy et al. |
| 2005/0015081 A1 | 1/2005 | Turovskiy et al. |
| 2005/0065508 A1 | 3/2005 | Johnson et al. |
| 2005/0085881 A1 | 4/2005 | Prakash et al. |
| 2005/0107783 A1 | 5/2005 | Tom et al. |
| 2005/0148836 A1 | 7/2005 | Kleen et al. |
| 2005/0159741 A1 | 7/2005 | Paul et al. |
| 2006/0264923 A1 | 11/2006 | Prakash et al. |
| 2006/0282069 A1 | 12/2006 | Prakash et al. |
| 2007/0027451 A1 | 2/2007 | Desinger et al. |
| 2007/0073282 A1 | 3/2007 | McGaffigan et al. |
| 2007/0123765 A1 | 5/2007 | Hetke et al. |
| 2007/0129715 A1 | 6/2007 | Eggers et al. |
| 2007/0135879 A1 | 6/2007 | McIntyre et al. |
| 2007/0142829 A1 | 6/2007 | Ahn et al. |
| 2007/0149964 A1 | 6/2007 | Kawabata et al. |
| 2007/0156048 A1 | 7/2007 | Panescu et al. |
| 2007/0156128 A1 | 7/2007 | Jimenez |
| 2007/0156132 A1 | 7/2007 | Drysen |
| 2007/0156133 A1 | 7/2007 | McDaniel et al. |
| 2007/0173680 A1 | 7/2007 | Rioux et al. |
| 2007/0173798 A1 | 7/2007 | Adams et al. |
| 2007/0173812 A1 | 7/2007 | Bonan et al. |
| 2007/0179375 A1 | 8/2007 | Fuimaono et al. |
| 2007/0179497 A1 | 8/2007 | Eggers et al. |
| 2007/0185478 A1 | 8/2007 | Cosentino |
| 2007/0191825 A1 | 8/2007 | Cronin et al. |
| 2007/0203551 A1 | 8/2007 | Cronin et al. |
| 2007/0208334 A1 | 9/2007 | Woloszko et al. |
| 2007/0208335 A1 | 9/2007 | Woloszko et al. |
| 2007/0208383 A1 | 9/2007 | Williams |
| 2007/0213700 A1 | 9/2007 | Davison et al. |
| 2007/0213703 A1 | 9/2007 | Naam et al. |
| 2007/0215163 A1 | 9/2007 | Harrington et al. |
| 2007/0219551 A1 | 9/2007 | Honour et al. |
| 2007/0225701 A1 | 9/2007 | O'Sullivan |
| 2007/0233057 A1 | 10/2007 | Konishi |
| 2007/0244529 A1 | 10/2007 | Choi et al. |
| 2007/0250053 A1 | 10/2007 | Fernald et al. |
| 2007/0250054 A1 | 10/2007 | Drake |
| 2007/0250055 A1 | 10/2007 | Johnson et al. |
| 2007/0250056 A1 | 10/2007 | Vanney |
| 2007/0255276 A1 | 11/2007 | Sliwa, Jr. et al. |
| 2007/0260235 A1 | 11/2007 | Podhajsky |
| 2007/0260237 A1 | 11/2007 | Sutton et al. |
| 2007/0270679 A1 | 11/2007 | Nguyen et al. |
| 2007/0270791 A1 | 11/2007 | Wang et al. |
| 2007/0276361 A1 | 11/2007 | Stevens-Wright et al. |
| 2007/0276362 A1 | 11/2007 | Rioux et al. |
| 2007/0282323 A1 | 12/2007 | Woloszko et al. |
| 2007/0282324 A1 | 12/2007 | Vaska et al. |
| 2007/0282325 A1 | 12/2007 | Young et al. |
| 2007/0287995 A1 | 12/2007 | Mayse |
| 2007/0287998 A1 | 12/2007 | Sharareh et al. |
| 2007/0293853 A1 | 12/2007 | Truckai et al. |
| 2007/0293854 A1 | 12/2007 | Pless et al. |
| 2007/0293855 A1 | 12/2007 | Sliwa, Jr. et al. |
| 2007/0299488 A1 | 12/2007 | Carr |
| 2008/0004614 A1 | 1/2008 | Burdette et al. |
| 2008/0004618 A1 | 1/2008 | Johnson et al. |

FOREIGN PATENT DOCUMENTS

| | | |
|---|---|---|
| WO | WO 93/20767 | 10/1993 |
| WO | WO 93/20768 | 10/1993 |
| WO | WO 95/01814 | 1/1995 |
| WO | WO 96/34571 | 11/1996 |
| WO | WO 97/48449 A1 | 12/1997 |
| WO | WO 97/48450 | 12/1997 |
| WO | WO 97/48451 | 12/1997 |
| WO | WO 99/56642 | 11/1999 |
| WO | WO 99/56643 | 11/1999 |
| WO | WO 99/56812 | 11/1999 |
| WO | WO 00/49957 | 8/2000 |
| WO | WO 00/57811 | 10/2000 |
| WO | WO 01/60235 | 8/2001 |
| WO | WO 02/078777 | 10/2002 |
| WO | WO 03/034932 | 5/2003 |
| WO | WO 03/039385 | 5/2003 |
| WO | WO 03/047043 | 6/2003 |
| WO | WO 03/088806 | 10/2003 |
| WO | WO 03/088858 | 10/2003 |
| WO | WO 2005/011049 | 2/2005 |

OTHER PUBLICATIONS

Urologix, Inc.—Medical Professionals: Targis Technology http://www.urologix.com/medical/technology.html; 3 pages.

International Search Report corresponding to European Application No. EP 06 00 9435.6, completed Jul. 6, 2006; mailed Jul. 13, 2006; 3 pages.

Official Action issued in the corresponding Japanese Application No. 2006-128689 dated Sep. 29, 2011.

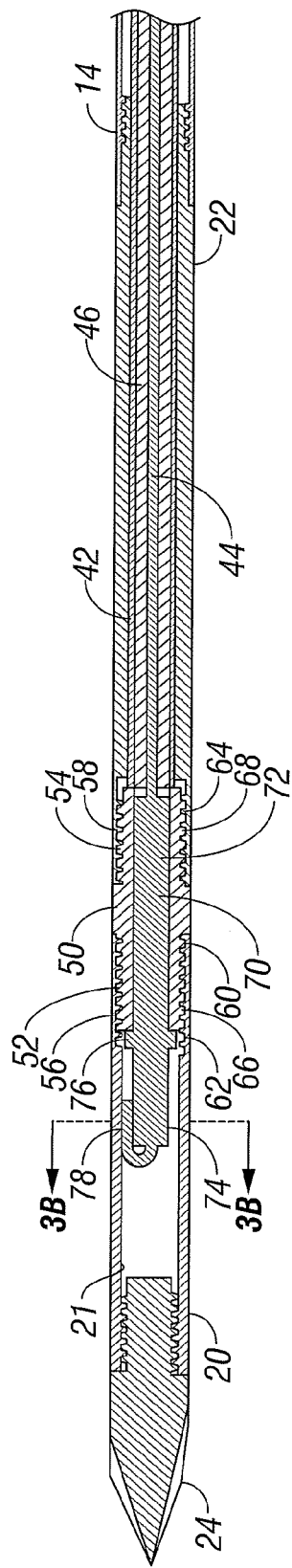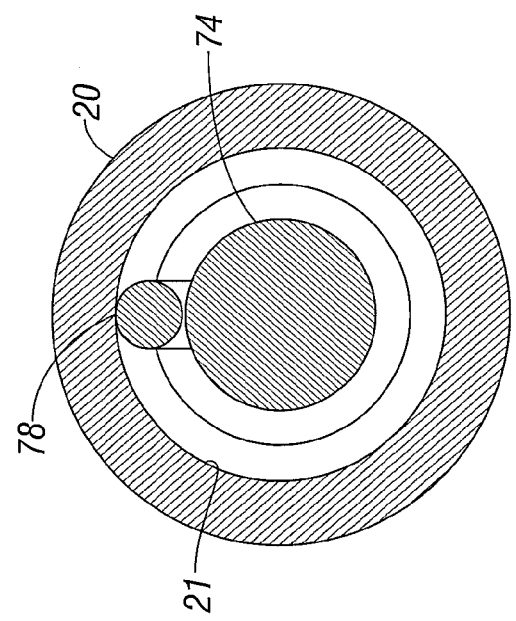
FIG. 3A
FIG. 3B

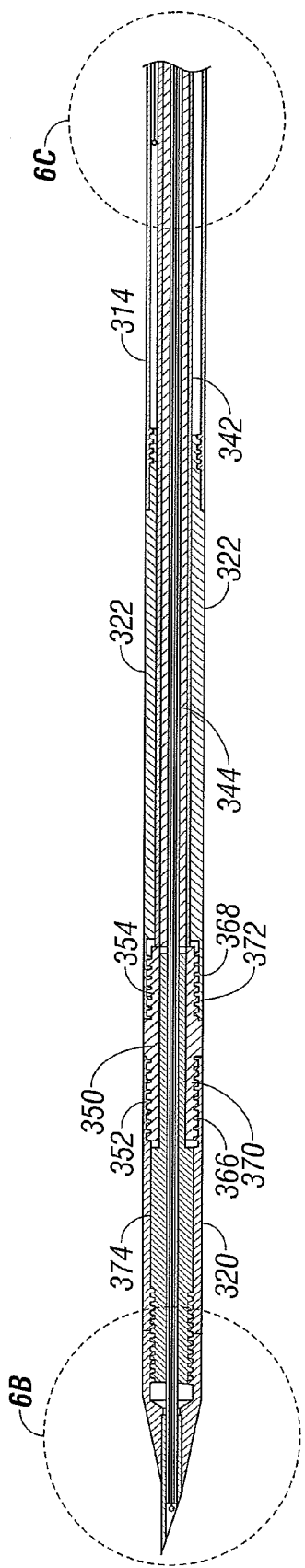
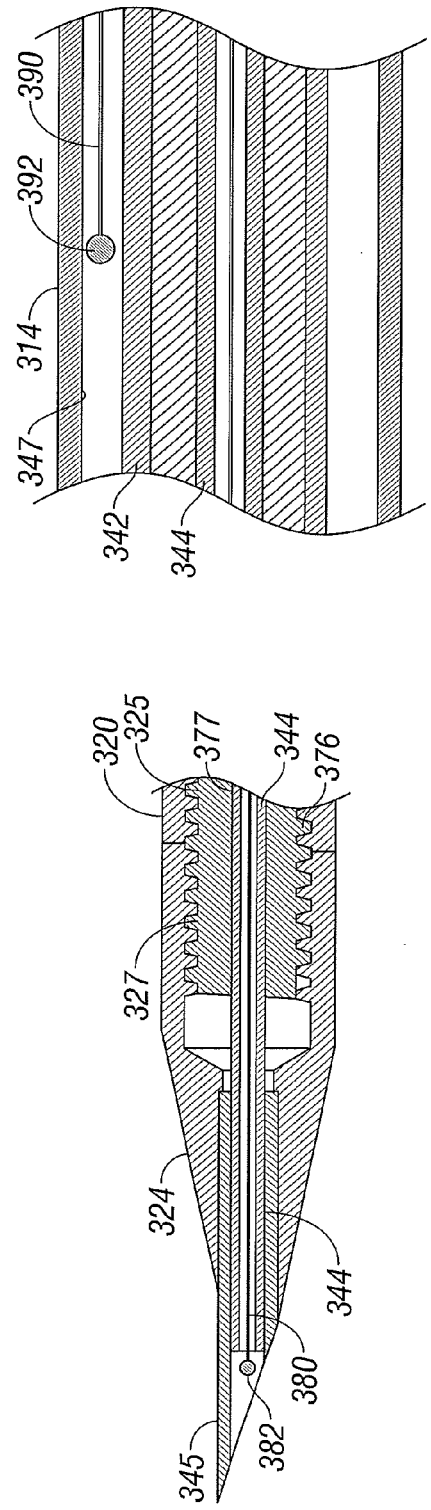
FIG. 6A
FIG. 6C
FIG. 6B

REINFORCED HIGH STRENGTH MICROWAVE ANTENNA

CROSS-REFERENCE TO RELATED APPLICATIONS

The present application is a continuation application of U.S. patent application Ser. No. 13/214,503, filed on Aug. 22, 2011, now U.S. Pat. No. 8,192,426, which is a continuation application of U.S. patent application Ser. No. 12/859,841, filed on Aug. 20, 2010, now U.S. Pat. No. 8,012,148, which is a continuation application of U.S. Pat. No. 7,799,019, filed on May 10, 2005, the entire contents of which are incorporated herein by reference.

FIELD

The described devices relate generally to microwave antenna probes and methods of their use, e.g., in tissue ablation applications. More particularly, the described devices relate to microwave antennas that may be inserted directly into tissue for diagnosis and treatment of diseases.

BACKGROUND

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control. This is partly why a more direct and precise method of applying microwave radiation has been sought.

Presently, there are several types of microwave probes in use, e.g., monopole, dipole, and helical. One type is a monopole antenna probe, which consists of a single, elongated microwave conductor exposed at the end of the probe. The probe is sometimes surrounded by a dielectric sleeve. The second type of microwave probe commonly used is a dipole antenna, which consists of a coaxial construction having an inner conductor and an outer conductor with a dielectric separating a portion of the inner conductor and a portion of the outer conductor. In the monopole and dipole antenna probe, microwave energy generally radiates perpendicularly from the axis of the conductor.

The typical microwave antenna has a long, thin inner conductor which extends along the axis of the probe and is surrounded by a dielectric material and is further surrounded by an outer conductor around the dielectric material such that the outer conductor also extends along the axis of the probe. In another variation of the probe, which provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or a combination thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

However, many types of malignancies are difficult to reach and treat using non-invasive techniques or by using invasive antenna probes designed to be inserted into a normal body orifice, i.e., an easily accessible body opening. These types of conventional probes may be more flexible and may also avoid the need to separately sterilize the probe; however, they are structurally weak and typically require the use of an introducer or catheter to gain access to within the body. Moreover, the addition of introducers and catheters necessarily increase the diameter of the incision or access opening into the body thereby making the use of such probes more invasive and further increasing the probability of any complications that may arise.

Structurally stronger invasive probes exist and are typically long, narrow, needle-like antenna probes which may be inserted directly into the body tissue to directly access a site of a tumor or other malignancy. Such rigid probes generally have small diameters that aid not only in ease of use but also reduce the resulting trauma to the patient. A convenience of rigid antenna probes capable of direct insertion into tissue is that the probes may also allow for alternate additional uses given different situations. However, such rigid, needle-like probes may experience difficulties in failing to provide uniform patterns of radiated energy; and may fail to provide uniform heating axially along and radially around an effective length of the probe. Accordingly, it may be difficult to otherwise control and direct the heating pattern when using such probes.

Accordingly, there remains a need for a microwave antenna probe that may help in overcoming the problems discussed above. There also exists a need for a microwave antenna probe that is structurally robust enough for direct insertion into tissue without the need for additional introducers or catheters while producing a controllable and predictable heating pattern.

BRIEF SUMMARY

The described methods and devices provide for microwave antenna probes and their method of use, e.g., in tissue ablation applications. In some variations, the microwave antenna assembly has proximal and distal radiating portions. An inner and an outer conductor extend through the proximal radiating portion, with the inner conductor disposed within the outer conductor. The inner conductor further extends at least partially into the distal radiating portion. A junction member separates the proximal and distal radiation sections with at least a portion of the junction member disposed between the proximal and distal radiating portions. A reinforcing member is disposed longitudinally at least partially within the junction member and provides additional stiffness to the junction member, thereby increasing the overall structural integrity of the assembly and allowing for easier direct insertion of the assembly into tissue. The microwave antenna assembly may also comprise a sensor selected from the group consisting of a temperature sensor, a pressure sensor, and a flow sensor. In some variations, the sensor is a temperature sensor. Methods for assembling the disclosed microwave antenna assemblies are also described.

In certain variations, the reinforcing member extends from the junction member into the distal radiating portion. In other variations, the inner conductor extends through the reinforcing member. The inner conductor can be affixed to the distal radiating portion or can otherwise be placed into electrical communication with the distal radiating portion. In yet other variations, the reinforcing member itself can be integrally formed with the inner conductor as a single piece. In further variations, the inner conductor and distal radiating portion itself are integrally formed as a single piece. The proximal radiating portion may also be a single piece, and in some variations, the proximal radiating portion has a variable wall thickness. The microwave antenna assembly may also be connected to a source of microwave energy.

In another variation the microwave antenna assembly is further provided with a thermocouple for localized temperature sensing, with the thermocouple junction being positioned e.g., along the distal radiating portion. In yet a further variation, the microwave assembly is further provided with a lumen extending through at least a portion of the proximal radiating portion, or proximal to the proximal radiating portion, and opening to the surface of the assembly, for e.g., to deliver therapeutic agents to tissue, to provide a thermocouple or other temperature sensor, to act as an aspiration port for delivery or removal of fluids, or for the delivery of transducers or sensors to measure or sense various characteristics of the surrounding tissue and/or antenna performance.

To improve the energy focus of the antenna assembly, an electrical choke may also be used in any of the variations described herein to contain returning currents to the distal end of the antenna assembly. The choke may be disposed on top of a dielectric material on the antenna proximal of the radiating section. The choke is preferably comprised of a conductive layer and may be further covered by a tubing or coating to force the conductive layer to conform to the underlying antenna.

Additionally, variations on the choke, the tubing or coating, any sealant layers, as well as other layers that may be disposed over the antenna assembly may be used. Certain layers, e.g., a heatshrink layer disposed over the antenna assembly, may have wires or strands integrated within the layer to further strengthen the antenna assembly. Kevlar wires, for instance, may be integrally formed into the layer and oriented longitudinally with the antenna axis to provide additional strength.

BRIEF DESCRIPTION OF THE DRAWINGS

FIG. 3A depicts a side sectional view of a microwave antenna assembly showing a junction member and reinforcing member according to one variation of the assemblies described herein;

FIG. 3B depicts a cross-sectional view of the assembly of FIG. 3A taken along the plane designated by line 3B-3B;

FIG. 6A depicts a cross-sectional view of a microwave antenna assembly showing a junction member and a reinforcing member according to a further variation of the microwave antenna assemblies described herein;

FIGS. 6B and 6C depict enlarged cross-sectional views of the distal end and proximal section, respectively, of the microwave antenna assembly of FIG. 6A;

DETAILED DESCRIPTION

Figure 1:
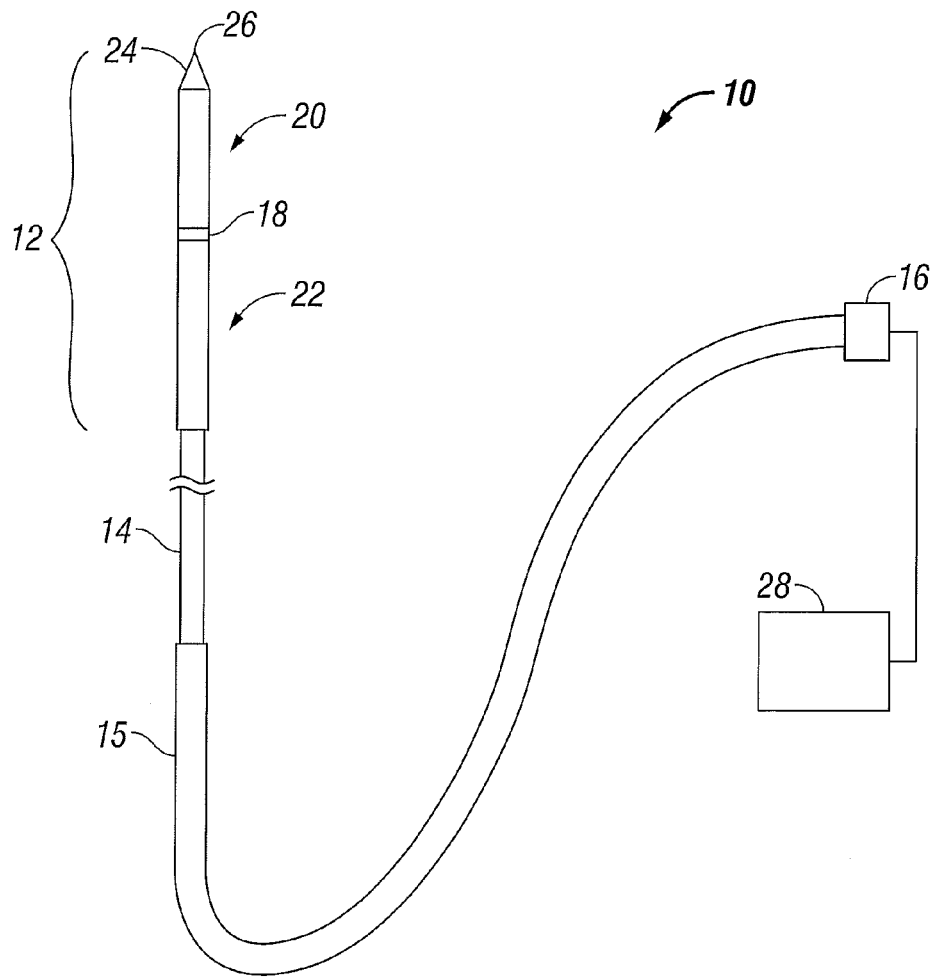
FIG. 1 shows a representative diagram of a variation of a microwave antenna assembly described herein.

During invasive treatment of diseased areas of tissue in a patient, trauma may be caused to the patient resulting in pain and other complications. Various microwave antenna assemblies, as described herein, are less traumatic than devices currently available and as described in further detail below, methods of manufacturing such devices are also described. Generally, the devices and assemblies described here allow for the direct insertion of a microwave antenna into tissue for the purposes of diagnosis and treatment of disease. FIG. 1 shows a representative diagram of a variation of a microwave antenna assembly 10. The antenna assembly 10 is generally comprised of radiating portion 12 that may be connected by shaft 14 via cable 15 to connector 16, which may further connect the assembly 10 to a power generating source 28, e.g., a generator or source of microwave energy. Assembly 10, as shown, is a dipole microwave antenna assembly, but other antenna assemblies, e.g., monopole helical, or leaky wave antenna assemblies, may also utilize the principles set forth herein. Distal portion 20 of radiating portion 12 preferably has a tapered end 24 that terminates at a tip 26 to allow for insertion into tissue with minimal resistance. In those cases where the radiating portion 12 is inserted into a pre-existing opening, tip 26 may be rounded or flat.

Figures 2A, 2B:
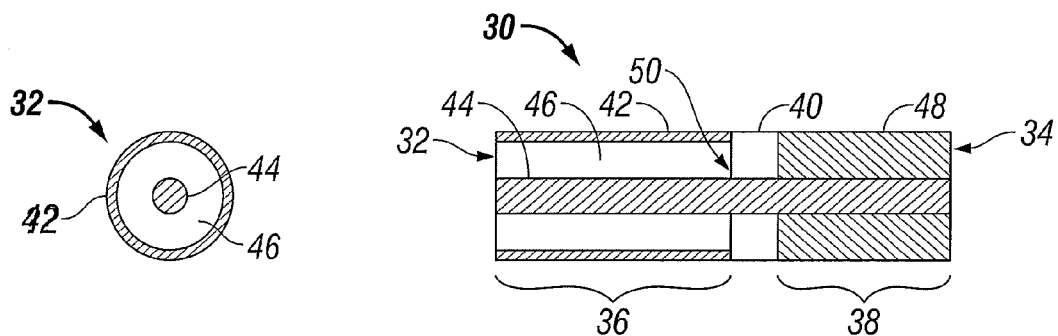
FIGS. 2A and 2B depict cross-sectional views of a conventional microwave antenna assembly.

In certain applications, a microwave antenna requires adequate structural strength to prevent bending of the antenna, e.g., where the antenna is directly inserted into tissue, where the antenna undergoes bending moments after insertion, etc. FIGS. 2A and 2B show an end view and a cross-sectional view, respectively, of a conventional dipole microwave antenna assembly 30. As seen, antenna assembly 30 has a proximal end 32 that may be connected to a shaft 14, as further discussed herein, and terminates at distal end 34. The radiating portion of antenna 30 comprises proximal radiating portion 36 and distal radiating portion 38. Proximal radiating portion 36 may typically have an outer conductor 42 and an inner conductor 44, each of which extends along a longitudinal axis. Between the outer and inner conductors 42 and 44 is typically a dielectric material 46, which is also disposed longitudinally between the conductors 42 and 44 to electrically separate them. A dielectric material may constitute any suitable dielectric material, including air. Distal portion 48 is also made from a conductive material, as discussed below. Proximal and distal radiating portions 36 and 38 align at junction 40, which is typically made of a dielectric material, and are also supported by inner conductor 44, which runs through junction opening 50 and at least partially through distal portion 48. The construction of conventional antenna assembly 30 however, is structurally weak at junction 40.

Accordingly, there are various configurations designed to increase the antenna strength. Such configurations include those described in U.S. patent application Ser. No. 10/052,848 filed Nov. 2, 2001, which is incorporated herein by reference in its entirety. One configuration involves placing the antenna assembly under a compressive load to stiffen the radiating portions. Another configuration involves mechanically fastening, e.g., in a screw-like manner, the radiating portions together to provide a joint that will withstand bending moments. A further configuration involves creating overlapping joints between the radiating portions of the antenna assembly to provide a high-strength antenna. Many of these configurations will generally include a junction member disposed between and separating the proximal and distal radiating portions. As further detailed herein, the devices and assemblies described here provide for reinforcement members of various configurations that are disposed within the junction members to further stiffen and strengthen the overall assembly, without compromising the functionality of the assembly or its ease of manufacture.

Antenna Assembly with Reinforced Junction Member

Generally, the antenna assembly 10 in FIG. 1 shows a variation where proximal radiating portion 22 is located proximally of distal radiating portion 20, with junction member 18 preferably located between the radiating portions. Shaft 14 may electrically connect antenna assembly 10 via cable 15 to generator 28 and usually comprises a coaxial cable made of a conductive metal that may be semi-rigid or flexible. Shaft 14 may also have a variable length from a proximal end of radiating portion 12 to a distal end of cable 15 ranging between about 1 to 10 inches. The shaft may be constructed of copper, gold, or other conductive metals with similar conductivity values, but shaft 14 is preferably made of stainless steel. The metals may also be plated with other materials, e.g., other conductive materials, to improve their properties, e.g., to improve conductivity or decrease energy loss, etc. A shaft 14, such as one made of stainless steel, preferably has an impedance of about 50Ω and to improve its conductivity, the stainless steel may be coated with a layer of a conductive material such as copper or gold. Although stainless steel may not offer the same conductivity as other metals, it does offer strength required to puncture tissue and/or skin. In many variations, the shaft will further include a cooling sheath that surrounds the coaxial cable, including but not limited to cooling sheath systems described in U.S. patent application Ser. No. 10/622,800, filed Jul. 18, 2003, and entitled "Devices and Methods for Cooling Microwave Antennas", now Pub. No. US 2005/0015081 A1, which is incorporated herein by reference in its entirety.

In operation, microwave energy having a wavelength, λ, is transmitted through antenna assembly 30 along both proximal and distal radiating portions 36 and 38. This energy is then radiated into the surrounding medium, e.g., tissue. The length of the antenna for efficient radiation may be dependent at least on the effective wavelength, λeff, which is dependent upon the dielectric properties of the medium being radiated into. Energy from the antenna assembly 30 radiates and the surrounding medium is subsequently heated. An antenna assembly 30 though which microwave energy is transmitted at a wavelength, λ, may have differing effective wavelengths, λeff, depending upon the surrounding medium, e.g., liver tissue, as opposed to, e.g., breast tissue. Also affecting the effective wavelength, λeff, are coatings that may be disposed over antenna assembly 30, as discussed further below.

FIGS. 3A-3B show sectional views of radiating portion 12. As seen, the radiating portion 12 comprises proximal radiating portion 22 and distal radiating portion 20. Proximal radiating portion 22 may typically have an outer conductor 42 and an inner conductor 44, each of which extends along a longitudinal axis. Between the outer and inner conductors 42 and 44 is typically a dielectric material 46, which is also disposed longitudinally between the conductors 42 and 44 to electrically separate them. A dielectric material may constitute any suitable dielectric material, including air. Distal portion 20 is also made from a conductive material, as discussed below. Proximal and distal radiating portions 22 and 20 align at junction member 50, which is typically made of a dielectric material, as is further discussed below. As seen, junction member 50 has first and second junction mating sections 52 and 54 that may be connected to distal and proximal portions 20 and 22, respectively. Junction member 50 is preferably comprised of any suitable dielectric material. Alternatively, a dielectric coating or layer may also be applied to the inside of channels 62 and 64 which contact junction member 50. First and second mating sections 52 and 54 may be threaded as shown by threads 56 and 58, respectively, such that the thread pitch on each section 52,54 is opposed to each other, i.e., the pitch angle of threading 56 may be opposite to the pitch angle of threading 58. Alternatively, the thread pitch on each section may be configured to be angled similarly for ease of antenna assembly. Distal portion 20 may have a receiving cavity or channel 62 which is threaded 66 at a predetermined pitch to correspond to the pitch and angle of the threading 66 on first mating section 52. Likewise, proximal portion 22 may have a receiving cavity or channel 64 which is threaded 68 at a predetermined pitch to correspond to the pitch and angle of the threading 58 on second mating section 54. Having opposed pitch angles may help to ensure a secure fit or joint when antenna assembly is assembled by screwing proximal portion 22 and distal portion 20 together onto junction member 50.

As can be seen, channel 60 extends axially through junction member 50 and receives reinforcing member 70 which is generally cylindrical and configured to be received within and extend through the channel 60. The reinforcing member is generally formed of a stronger and stiffer material than the junction member and thus reinforces the junction member. In the variation depicted the reinforcing member is integrally formed with inner conductor 44 and includes central section 72 that resides within junction member 50 and a distal section 74 that extends from the junction member distally into the distal radiating portion. Wire 78 extends distally from section 74 and is in electrical contact with the inner perimeter 21 of the distal radiating section 20. In this configuration, the reinforcing member thus functions to extend the inner conductor through the junction member and into the distal radiating section. The combination of the inner conductor 44, reinforcing member 70 and terminal wire 78 into a single piece has manufacturing and assembly advantages. The terminal wire 78 can be bent such that upon insertion into the distal radiating portion, it comes into contact with the perimeter 21. The piece can further include stop 76, which retains reinforcing member 70 against junction member 50 and prevents it from moving proximally relative to the reinforcing member. In alternative configurations, the reinforcing member can be a separate piece that allows for passage of the inner conductor through to the distal section. In such alternative configurations, the reinforcing member need not be electrically conductive and in many configurations it may be desirable for the reinforcing member to be formed of a dielectric material. This material, for example, may be chosen so as to retain optimal antenna characteristics.

Figure 4A:
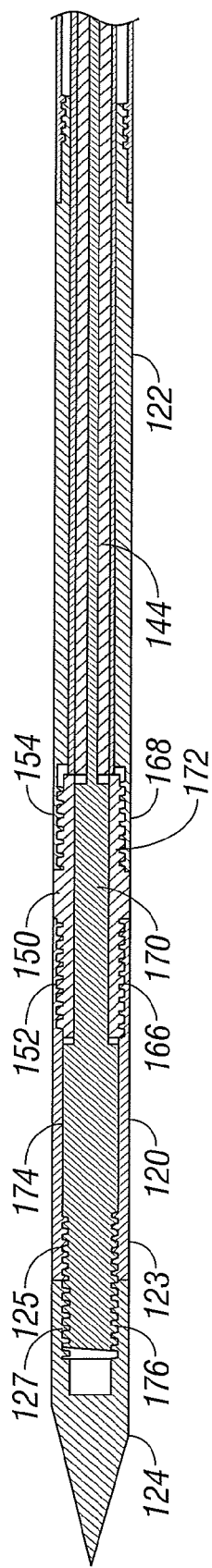
FIGS. 4A and 4B depict side and perspective sectional views, respectively, of a microwave antenna assembly showing a junction member and reinforcing member according to another variation of the described microwave antenna assemblies.
Figure 4B:
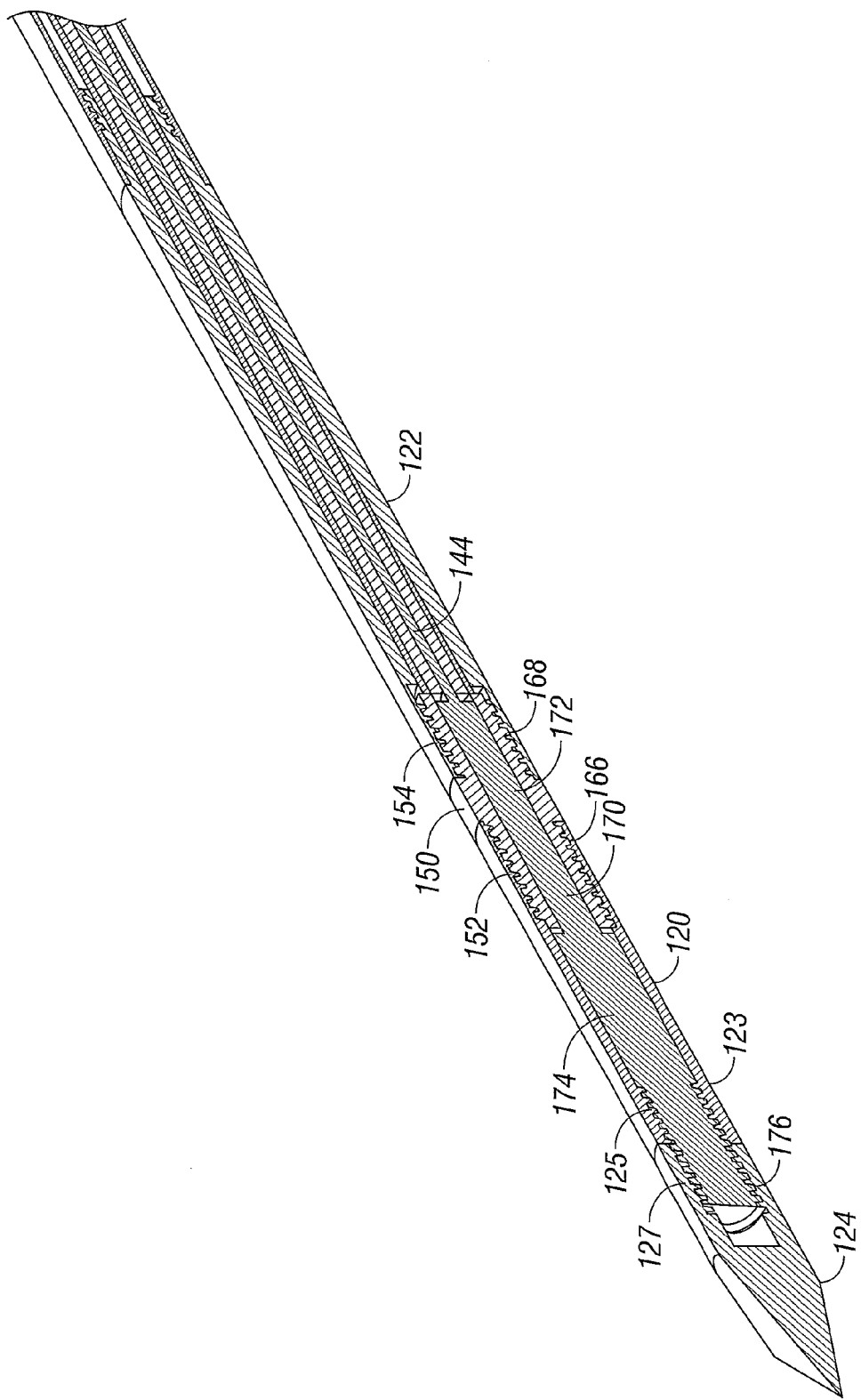

FIGS. 4A and 4B show another variation of a reinforced microwave antenna assembly. In this variation, reinforcing member 170 is again integrally formed with inner conductor 144 and includes central section 172 that resides within junction member 150. Junction member 150 is similar to junction member 50 of FIGS. 3A-3B in that it includes threaded first and second mating sections 152 and 154, that are screwed on to internal threads 166 and 168 of distal and proximal radiating sections 120 and 122. Reinforcing member 170 also includes a distal section 174 that extends distally from the junction member into the distal radiating portion. Distal section 174 is threaded 176 at its terminal end. Distal radiating section 120 is formed of tapered distal tip 124 (although shown as tapered, it need not be so) and section 123 that each have internal threads 125 and 127, respectively, that are aligned to both engage the threaded portion 176 of the reinforcing member, as shown. This allows the distal section 174 to be screwed into the distal radiating portion, which both provides for an electrical connection between inner conductor 144 and distal radiating portion, as well as providing for increased strength and rigidity to the distal radiating portion.

Figure 8:
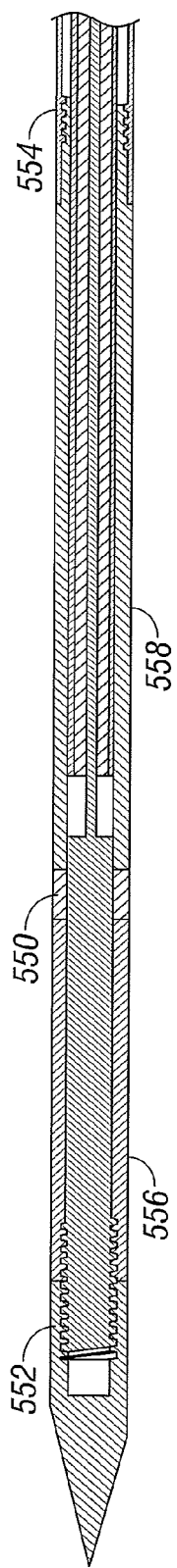
FIG. 8 depicts a cross-sectional view of a microwave antenna assembly without threaded mating sections adjacent to the junction member.

FIG. 8 depicts another variation of a suitable antenna assembly, which is similar in most respects to FIGS. 4A and 4B, except that it lacks threaded first and second mating 10 sections adjacent to the junction member 550. In this variation, the antenna assembly is held together by the distal and proximal threads. That is, distal section 556 is threaded 552 at its terminal end. Similarly, proximal section 558 is threaded at its terminal end 554.

Figure 5:
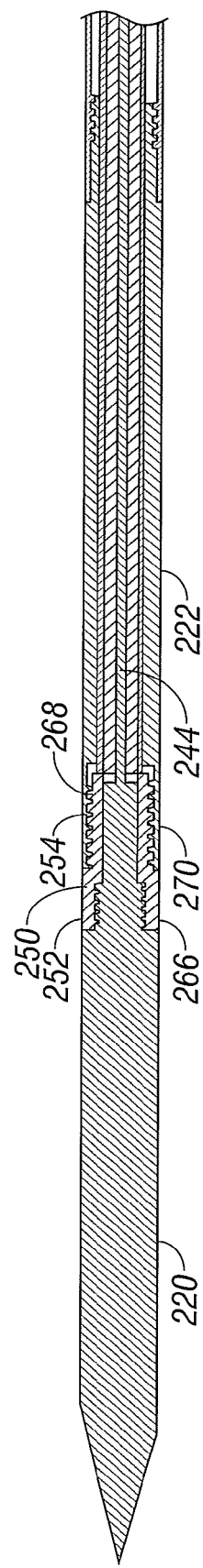
FIG. 5 depicts a cross-sectional view of a microwave antenna assembly showing a junction member and reinforcing member according to yet another variation of the microwave antenna assemblies described herein.

FIG. 5 shows a further variation of a reinforced microwave antenna assembly. In this variation, the entire distal radiating section 220 is integrally formed with reinforcing member 270 and inner conductor 244. Reinforcing member 270 resides within junction member 250 with distal radiating section extending distally from reinforcing member 270. Junction member 250 includes threaded first and second mating sections 252 and 254. Mating section 254 of junction member 250 is externally threaded as shown, and is screwed on to internal threads 268 of proximal radiating section 222. Mating section 252, however, is internally threaded and is screwed on to externally threaded section 266 of junction member 250. In addition to reinforcing junction member 250, this configuration provides for continuous electrical communication of the inner conductor to the distal radiating portion.

Antenna Assembly with Reinforced Junction Member and Thermocouple

FIGS. 6A-6C show yet a further variation of a reinforced microwave antenna assembly. In this variation, reinforcing member 370 is similar to reinforcing member 170 of FIGS. 4A and 4B in that it also includes a central section 372 that resides within junction member 350. Junction member 350 is similar to junction members 50 and 150 of FIGS. 3A-3B and 4 in that it includes threaded first and second mating sections 352 and 354, which are screwed on to internal threads 366 and 368 of distal and proximal radiating sections 320 and 322. Reinforcing member 370 includes a distal section 374 that extends distally from the junction member into the distal radiating portion. Distal section 374 is threaded 376 at its terminal end. Distal radiating section 320 is formed of tapered distal tip 324 and section 322 that each have internal threads 325 and 327, respectively, that are aligned to both engage the threaded portion 376 of the reinforcing member, as shown. This allows the distal section 374 to be screwed into the distal radiation portion, providing for increased strength and rigidity to the distal radiating portion. Unlike reinforcing member 170, however, reinforcing member 370 contains a central channel 377 that receives and allows passage of inner conductor 344 through junction member 350. As shown most clearly in FIG. 6B, inner conductor 344 extends the length of the assembly to its distal tip 324 where it emerges from the assembly. Inner conductor 344 terminates in needle tip 345. As also shown, the inner conductor is hollow, allowing passage of thermocouple 380 which is positioned within the inner conductor lumen with thermocouple junction 382 at the tip. While tip 382 is shown as rounded or blunt, it need not be. That is, tip 382 can have any suitable geometry, e.g., it can be sharp, or have a piercing distal tip. In addition, thermocouple 380 may be slidable within the antenna, and may even be configured to extend out of the distal end of the antenna. Like the tip 382, the thermocouple 380 may have any suitable geometry. For example, it can be configured, such that when it is deployed out of the distal end of the antenna, it assumes a curved configuration. The thermocouple can provide and monitor localized temperature readings of tissue when the device is operated. Other monitoring devices can be deployed through the inner conductor lumen, including but not limited to sensors and transducers that respond to, e.g., electrical, magnetic, optical, thermal or mechanical stimulus. The inner conductor lumen can also be used to deliver fluids, such as irrigation fluids, or therapeutics, or to remove tissue or fluid samples. Additional thermocouples or other monitoring devices can also be provided. For example, as shown most clearly in FIG. 6C, thermocouple 390 having thermocouple junction 392 is positioned proximal of proximal radiating section 322 in lumen 347 between outer conductor 342 and shaft 314. Lumen 347 can contain e.g., a cooling fluid and thermocouple 390 can be used to measure the temperature of such cooling fluid.

Antenna Assembly with Reinforced Junction Member and Cooling Chamber

Figure 7:
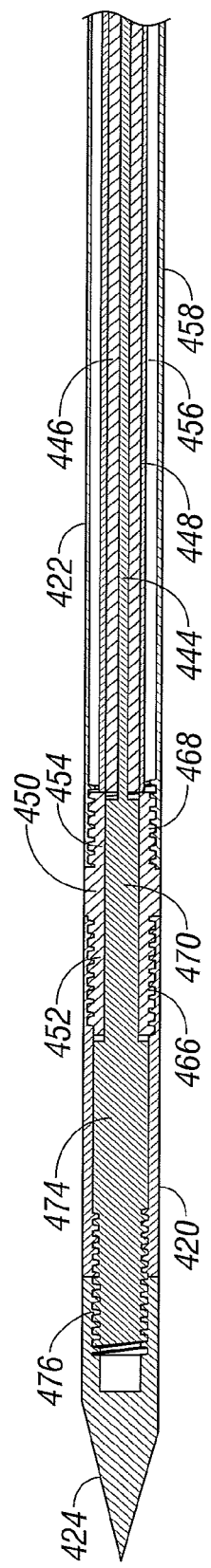
FIG. 7 depicts a cross-sectional view of a microwave antenna assembly showing a cooling chamber according to a further variation of the microwave antenna assemblies described herein.

FIG. 7 shows another variation of a reinforced microwave antenna assembly. In this variation, reinforcing member 470 is similar to reinforcing member 170 of FIG. 4A. Junction member 450 is also similar to junction member 150 of FIG. 4A in that it includes threaded first and second mating sections 452 and 454, which are screwed on to internal threads 466 and 468 of distal and proximal radiating sections 420 and 422. Reinforcing member 470 includes a distal section 474 that extends distally from the junction member into the distal radiating portion. Distal section 474 is threaded 476 at its terminal end. Distal radiating section 420 terminates with tapered distal tip 424 (although, as noted above, in some situations, the distal tip need not be tapered).

A dielectric 446 is positioned longitudinally between inner conductor 444 and outer conductor 448 to electrically separate them. In this variation, a cooling tube 456 is positioned longitudinally adjacent to outer conductor 448, and a cooling jacket 458 is positioned longitudinally adjacent to cooling tube 456, making up a cooling chamber. While not shown if FIG. 7, the proximal end of the cooling tube is connected to a source of cooling fluid. The cooling fluid passes through the cooling tube 456 (e.g., a polyimide tube or the like) to cool down the tissue immediately adjacent to cooling jacket 458 to prevent burning or other tissue damage. The cooling fluid may be any suitable fluid (e.g., water, saline, etc.).

Materials and Methods

Junction members used in the antenna assemblies described herein are preferably made of a dielectric material such as a ceramic or other suitable dielectric. Illustrative examples of suitable dielectric materials include, but are not limited to $Al_2O_3$, Boron Nitride, stabilized Zirconia, air, and the like. Alternatively, junction members can made of a metal and sufficiently coated with a dielectric or polymer (e.g., high temperature polymers like polyimide or Ultem™ provided the dielectric coating is sufficiently thick to provide adequate insulation. To prevent energy from conducting directly into the tissue during use, a dielectric layer having a thickness between about 0.0001 to 0.025 inches may be coated directly over the antenna assembly. The dielectric coating may increase the radiated energy and is preferably made from a ceramic material, such as $Al_2O_3$, $TiO_2$, or the like, and may also be optionally further coated with a lubricious material such as Teflon™, polytetrafluoroethylene (PTFE), or fluorinated ethylene propylene (FEP), etc. In addition to the dielectric coating, a sealant layer may also be coated either directly over the antenna assembly, or preferably over the dielectric layer to provide a lubricious surface for facilitating insertion into a patient as well as to prevent tissue from sticking to the antenna assembly. The sealant layer may be any variety of polymer, but is preferably a thermoplastic polymer and may have a thickness varying from a few angstroms to as thick as necessary for the application at hand. The sealant layer may be made from a variety of thermoplastic polymers, e.g., heat shrink polymers, such as polyethylene (PE), polyethylene terephthalate (PET), polytetrafluoroethylene (PTFE), fluorinated ethylene propylene (FEP), perfluoroalkoxy (PFA), chlorotrifluoroethylene (CTFE), ethylene chlortrifluoroethylene (ECTFE), and ethylene tetrafluoroethylene (ETFE). Varying these coating thicknesses over antenna assembly may vary the effective wavelengths, $\lambda$eff, of the radiation being transmitted by the antenna. Thus, one may vary the coating thicknesses over the assembly to achieve a predetermined effective wavelength depending upon the desired results.

A preferable method of optimizing the amount of radiated energy from the assembly may include adjusting the length of proximal radiating portion to correspond to a length of $n\lambda/4$ (where n is any integer) of the radiation being transmitted through assembly, and likewise adjusting a cumulative (or overall) length of distal radiating portion and junction to also correspond to a length of $n\lambda/4$. Adjusting the lengths of proximal and distal radiating portions to correspond to the wavelength of the transmitted microwaves may be done to optimize the amount of radiated energy and accordingly, the amount of the medium or tissue that is subsequently heated. The actual lengths of proximal and distal radiating portions may, of course, vary and is not constrained to meet any particular $n\lambda/4$ length. When an antenna assembly is radiating energy, the ablation field is variable 3-dimensionally and may be roughly spherical or ellipsoidal, which centers on the junction member and extends to the ends of the proximal and distal radiating portions.

The location of the distal tip may be proportional to a distance of $n\lambda/4$ of the radiation being transmitted through the assembly. However, since the distal tip typically terminates at tapered end, the angled surface of taper may be taken into account. Thus, the total distance along the outer surfaces of the junction member and distal radiating portion (including any tapered end) may accord to the distance of $n\lambda/4$. The length of proximal radiating portion may also accord to the distance of $n\lambda/4$, as above. Although it is preferable to have the length of the radiating portion of the antenna accord with a distance of the wavelength, $\lambda$, it is not necessary for operation of the device, as described above. That is, an antenna assembly having a radiating portion with a length in accordance with a first wavelength may generally still be used for transmitting radiation having a second wavelength, or third wavelength, or so on, although with a possible reduction in efficiency. Also, while the variations described above are related to dipole antenna assemblies, monopole antenna assemblies are also contemplated.

To improve the energy focus of an antenna assembly, an electrical choke may also be used to contain returning currents to the distal end of the antenna, as is described U.S. patent application Ser. No. 10/052,848 filed Nov. 2, 2001, now U.S. Pat. No. 6,878,147, which is incorporated herein by reference in its entirety. Generally, the choke may be disposed on the antenna proximal of the radiating section. The choke is preferably placed over a dielectric material, which may be disposed over the antenna. The choke is preferably a conductive layer and may be further covered by a tubing or coating to force the conductive layer to conform to the underlying antenna, thereby forcing an electrical connection (or short) more distally and closer to the radiating section. The electrical connection between the choke and the underlying antenna may also be achieved by other connection methods such as soldering, welding, brazing, crimping, use of conductive adhesives, and the like.

Additional steps may optionally be taken to further increase the strength of an antenna assembly by altering any of the layers, such as sealant layer or any of the other heat-shrink layers discussed above. Wires or strands may be formed within, or on, the layers to add strength and are preferably orientated longitudinally along the length of the antenna such that the bending strength of the antenna is increased. The layers may be formed over the outer conductor, as described above, and the wires may be made of any high-strength material, e.g., Kevlar, metals, etc. Metal wires may be used, provided they are insulated.

Antenna Deployment

As described above, the microwave antenna may be inserted directly into the tissue and into the lesion to be treated. However, during insertion, the antenna may encounter resistance from some areas of tissue, particularly in some tissue found, e.g., in the breast. When the microwave antenna encounters resistance, if force were applied, tissue damage may result or the target tissue may be inadvertently pushed away due to the differential density of the target tissue relative to the surrounding tissue. Therefore, RF energy may also be utilized with the microwave antenna for facilitating deployment within the tissue.

In use, the RF energy may be simply left on the entire time the antenna is advanced through the tissue, or it may be applied or turned on only as needed as the antenna encounters resistance from the tissue. With the RF energy activated, the antenna may be further advanced utilizing the RF energy to cut through the obstructive tissue. Once the antenna has been desirably positioned within a lesion or region of tissue, the RF energy, if on, may be switched off and the microwave energy may be switched on to effect treatment.

In certain variations, the assembly may use RF energy at the distal tip of the antenna as a cutting mechanism during antenna deployment. The microwave antenna is preferably covered with some insulative material along most of its length, but distal tip may be uninsulated such that the FW energy may be applied thereto through the inner conductor. To utilize the RF energy cutting mechanism at the distal tip, the inner conductor may be made from Nitinol, Tungsten, stainless steel, or some other conductive metal.

The antenna assembly may be electrically connected to an RF generator that provides the RF energy to the distal tip during placement and positioning of the antenna within the tissue or lesion. After the antenna has been desirably positioned within the lesion, the connector may be disconnected from the RF cable and attached to a microwave generator via a microwave cable to provide the microwave energy for effecting treatment to the tissue.

Alternatively, given the small amount of surface area of the distal tip of the assembly, a low power FW generator may be utilized and can be built into an integral unit along with the microwave generator. Alternatively, an optional RF generator may be physically separated from the microwave generator and may be electrically connected as a separate unit to the antenna.

Aside from the illustrations of possible antenna deployment methods and devices described above, other variations for deployment and insertion into tissue may be utilized. Potential other methods and devices for antenna deployment and insertion may be found in U.S. patent application Ser. No. 10/272,314, filed Sep. 15, 2002, and entitled "Microwave Antenna Having A Curved Configuration", now U.S. Patent Application Pub. No. US 2003/0195499 A1, which is commonly owned and is incorporated herein by reference in its entirety.

Method of Use

In using a microwave antenna, several different methods may be utilized, including the use of single or multiple antennas, as is further described U.S. patent application Ser. No. 10/052,848 filed Nov. 2, 2001, now U.S. Pat. No. 6,878,147, which is incorporated herein by reference in its entirety.

The applications of the antenna assemblies and methods of making the assemblies discussed above are not limited to microwave antennas used for hyperthermic, ablation, and coagulation treatments but may include any number of further microwave antenna applications. Modification of the above-described assemblies and methods for carrying out the invention, and variations of aspects of the invention that are obvious to those of skill in the art are intended to be within the scope of the claims.

What is claimed:

1. A microwave antenna assembly, comprising:
    a radiating portion configured to operably couple to a source of microwave energy via a cable assembly, the radiating portion comprising:
        a proximal radiating portion including an outer conductor coaxially disposed around an inner conductor, the inner and outer conductors separated by a dielectric material; and
        a distal radiating portion disposed distally of the proximal radiating portion, the inner conductor longitudinally extending at least partially within the distal radiating portion;
    a choke disposed proximal of the proximal radiating portion;
    a cooling fluid chamber coaxially disposed around the outer conductor and configured to receive cooling fluid therein; and
    a thermocouple disposed within the radiating portion and configured to sense temperature within the radiating portion.

2. The microwave antenna assembly according to claim 1, further comprising a second thermocouple configured to sense temperature of tissue local to the radiating portion.

3. The microwave antenna assembly according to claim 1, wherein the thermocouple is disposed within the cooling fluid chamber.

4. The microwave antenna assembly according to claim 3, wherein the thermocouple is configured to sense a temperature of cooling fluid within the cooling fluid chamber.

5. The microwave antenna assembly according to claim 1, wherein the thermocouple is disposed proximal of the distal radiating portion.

6. The microwave antenna assembly according to claim 1, wherein the thermocouple includes a blunt distal tip.

7. The microwave antenna assembly according to claim 1, wherein the thermocouple extends distally at least partially along a longitudinal length of the radiating portion and terminates in a thermocouple junction.

8. The microwave antenna assembly according to claim 1, wherein the thermocouple is at least partially disposed within the inner conductor.

9. The microwave antenna assembly according to claim 1, further comprising a junction member having a longitudinal thickness, wherein at least a portion of the junction member is disposed between the proximal and distal radiating portions such that the inner conductor longitudinally extends therethrough.

10. The microwave antenna assembly according to claim 9, further comprising a reinforcing member disposed longitudinally at least partially within the junction member and having a diameter greater than a diameter of the inner conductor to provide increased stiffness to the junction member.

11. A microwave ablation system, comprising:
    a source of microwave energy configured to generate microwave energy;
    a microwave antenna assembly operably coupleable to the source of microwave energy, the microwave antenna assembly comprising:
        a radiating portion configured to deliver microwave energy to tissue, the radiating portion comprising:
            a proximal radiating portion including an outer conductor coaxially disposed around an inner conductor, the inner and outer conductors separated by a dielectric material;
            a distal radiating portion disposed distally of the proximal radiating portion, the inner conductor longitudinally extending at least partially within the distal radiating portion; and
            a choke disposed proximal of the proximal radiating portion;
    a cable assembly configured to operably couple the microwave antenna assembly to the source of microwave energy;
    a cooling fluid chamber coaxially disposed around the outer conductor and configured to receive cooling fluid therein; and
    a thermocouple disposed within the radiating portion and configured to sense temperature within the radiating portion.

12. The microwave ablation system according to claim 11, wherein the cable assembly includes a connector assembly disposed on one end thereof configured to operably couple the cable assembly to the source of microwave energy.

13. A microwave antenna assembly, comprising:
    a radiating portion configured to operably couple to a source of microwave energy via a cable assembly, the radiating portion comprising:

a proximal radiating portion including an outer conductor coaxially disposed around an inner conductor, the inner and outer conductors separated by a dielectric material and longitudinally extending at least partially within the proximal radiating portion;

a distal radiating portion disposed distally of the proximal radiating portion, the inner conductor longitudinally extending at least partially within the distal radiating portion; and an electrically conductive member coaxially disposed around at least the inner conductor;

a cooling fluid chamber coaxially disposed around the outer conductor and configured to receive cooling fluid therein; and a thermocouple disposed within the radiating portion and configured to sense temperature within the radiating portion.

* * * * *